United States Patent
Ishiyama et al.

(10) Patent No.: US 9,610,462 B2
(45) Date of Patent: Apr. 4, 2017

(54) PARTICLE BEAM TREATMENT APPARATUS

(71) Applicant: Kabushiki Kaisha Toshiba, Minato-Ku (JP)

(72) Inventors: Hiroshi Ishiyama, Yokohama (JP); Teppei Ukegawa, Yokohama (JP); Kentaro Matsui, Yokohama (JP); Yuuji Takiguchi, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 14/886,295

(22) Filed: Oct. 19, 2015

(65) Prior Publication Data

US 2016/0107001 A1 Apr. 21, 2016

(30) Foreign Application Priority Data

Oct. 21, 2014 (JP) .................................. 2014-214920

(51) Int. Cl.
*A61N 5/10* (2006.01)

(52) U.S. Cl.
CPC .... *A61N 5/1081* (2013.01); *A61N 2005/1074* (2013.01); *A61N 2005/1087* (2013.01)

(58) Field of Classification Search
CPC ..................... A61N 5/1081; A61N 2005/1074
USPC ............ 250/396 R, 397, 492.1, 492.3; 600/1
See application file for complete search history.

(56) References Cited

U.S. PATENT DOCUMENTS

| 2015/0144811 A1* | 5/2015 | Bergfjord | A61N 5/01 250/522.1 |
| 2015/0265230 A1* | 9/2015 | Matsuzawa | A61B 6/035 378/197 |

FOREIGN PATENT DOCUMENTS

JP 2014-113419 6/2014

* cited by examiner

*Primary Examiner* — Nicole Ippolito
(74) *Attorney, Agent, or Firm* — Oblon, McClelland, Maier & Neustadt, L.L.P.

(57) ABSTRACT

A particle beam treatment apparatus including a rotating gantry that revolves and displaces an irradiation port for irradiating a radiation treatment room provided inside of the rotating gantry with a charged particle beam comprises: a gantry body portion forming the rotating gantry; a mounted magnet; a displacement meter or an acceleration meter; and a control mechanism. The mounted magnet is connected to the gantry body portion with an intermediation of a magnet support, and guides the charged particle beam to the irradiation port. The displacement meter or the acceleration meter is provided to the mounted magnet, and measures a displacement or an acceleration of the mounted magnet. The control mechanism controls a position of the mounted magnet in a direction so as to reduce the displacement or the acceleration with at least a single degree of freedom measured by the displacement meter or the acceleration meter.

6 Claims, 4 Drawing Sheets

PARTICLE BEAM TREATMENT APPARATUS

CROSS-REFERENCE TO RELATED APPLICATIONS

This application is based upon and claims the benefit of priority from Japanese Patent application No. 2014-214920, filed on Oct. 21, 2014, the entire contents of each of which are incorporated herein by reference.

BACKGROUND OF THE INVENTION

Field of the Invention

An embodiment of the present invention relates to a particle beam treatment apparatus that irradiates an affected area of a patient with a charged particle beam to treat the affected area.

Description of the Related Art

A particle beam treatment technique of setting an irradiation target center (isocenter) to an affected area (such as a cancer-affected area) of a patient and irradiating the affected area with an ion beam of protons, carbon ions, or the like has been widely known.

For example, a particle beam treatment apparatus used for this treatment includes an ion beam generation apparatus, a beam transport system, and an irradiation apparatus installed in a rotating gantry.

An ion beam accelerated by the ion beam generation apparatus reaches the irradiation apparatus through the beam transport system, and an affected area of a patient is irradiated with the ion beam from the irradiation apparatus. On this occasion, the irradiation apparatus rotates around the patient along with a rotation of the rotating gantry, whereby the irradiation apparatus can irradiate the affected area with the ion beam on the basis of an irradiation angle determined by a treatment plan. In order to reduce damage to normal tissue around the affected area by the ion beam, it is necessary to precisely irradiate the affected area with the ion beam. For this purpose, it is important to perform precise positioning of a particle beam irradiation unit and precise positioning of the affected area of the patient with respect to the particle beam irradiation unit.

In general, a gantry body portion to which the irradiation apparatus is provided has a structure with rigidity that is sufficient to suppress a displacement of a magnet mounting portion and precisely irradiate the affected area with the ion beam. Such a conventional technique is disclosed in, for example, Japanese Patent Laid-Open No. 2014-113419.

In the rotating gantry of the above-mentioned conventional technique, if the rigidity of the gantry body portion is not sufficient, the displacement of the magnet mounting portion and three-dimensional whirling accuracy (irradiation target center accuracy) of a position of irradiation from the irradiation apparatus to the irradiation target center may have variations of about a few millimeters along with a rotation of the rotating gantry. As a result, there arises a problem that an enormous amount of time is required for positioning of the patient at the time of treatment irradiation, depending on the irradiation angle.

If a thickness of the gantry body portion is increased or a reinforcement member is added in order to enhance the rigidity of the body portion, increase in weight and manufacturing cost occurs. In addition, such increase in weight leads to increase in moment of inertia, so that braking time in emergency situations may become longer.

SUMMARY OF THE INVENTION

It is an object of the present invention to provide a particle beam treatment apparatus capable of making irradiation target center accuracy higher.

In order to achieve the above-mentioned object, an embodiment of the present invention provides a particle beam treatment apparatus including a rotating gantry that revolves and displaces an irradiation port for irradiating a radiation treatment room provided inside of the rotating gantry with a charged particle beam, the apparatus comprising: a gantry body portion forming the rotating gantry; a mounted magnet; a displacement meter or an acceleration meter; and a control mechanism. The mounted magnet is connected to the gantry body portion with an intermediation of a magnet support, and guides the charged particle beam to the irradiation port. The displacement meter or the acceleration meter is provided to the mounted magnet, and measures a displacement or an acceleration of the mounted magnet. The control mechanism controls a position of the mounted magnet in a direction so as to reduce the displacement or the acceleration with at least a single degree of freedom measured by the displacement meter or the acceleration meter.

An embodiment of the present invention can provide a particle beam treatment apparatus capable of making irradiation target center accuracy higher.

DETAILED DESCRIPTION OF THE PREFERRED EMBODIMENT

Hereinafter, an embodiment of the present invention is described with reference to the attached drawings.

Figure 1:
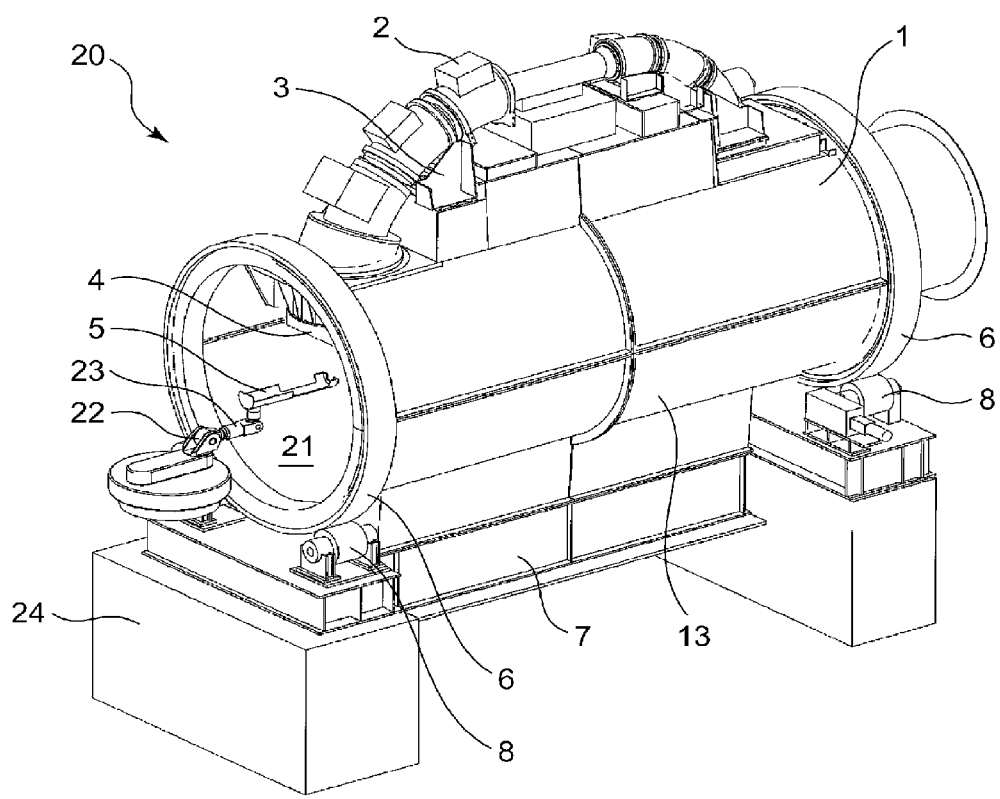
FIG. 1 is a perspective view illustrating an embodiment of a particle beam treatment apparatus according to the present invention.
Figure 2:
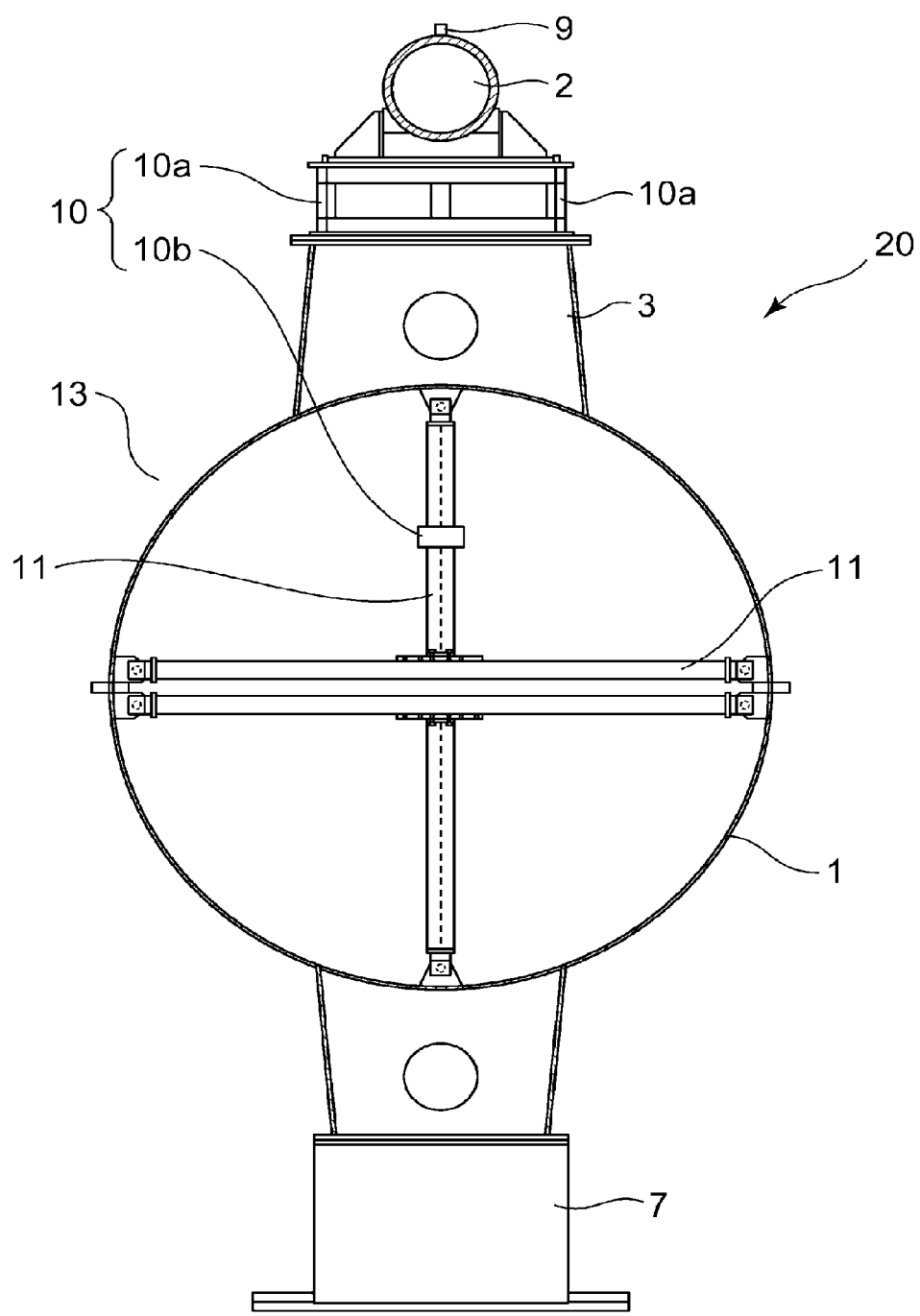
FIG. 2 is a cross-sectional view taken in a central portion of the particle beam treatment apparatus illustrated in FIG. 1.
Figure 3:
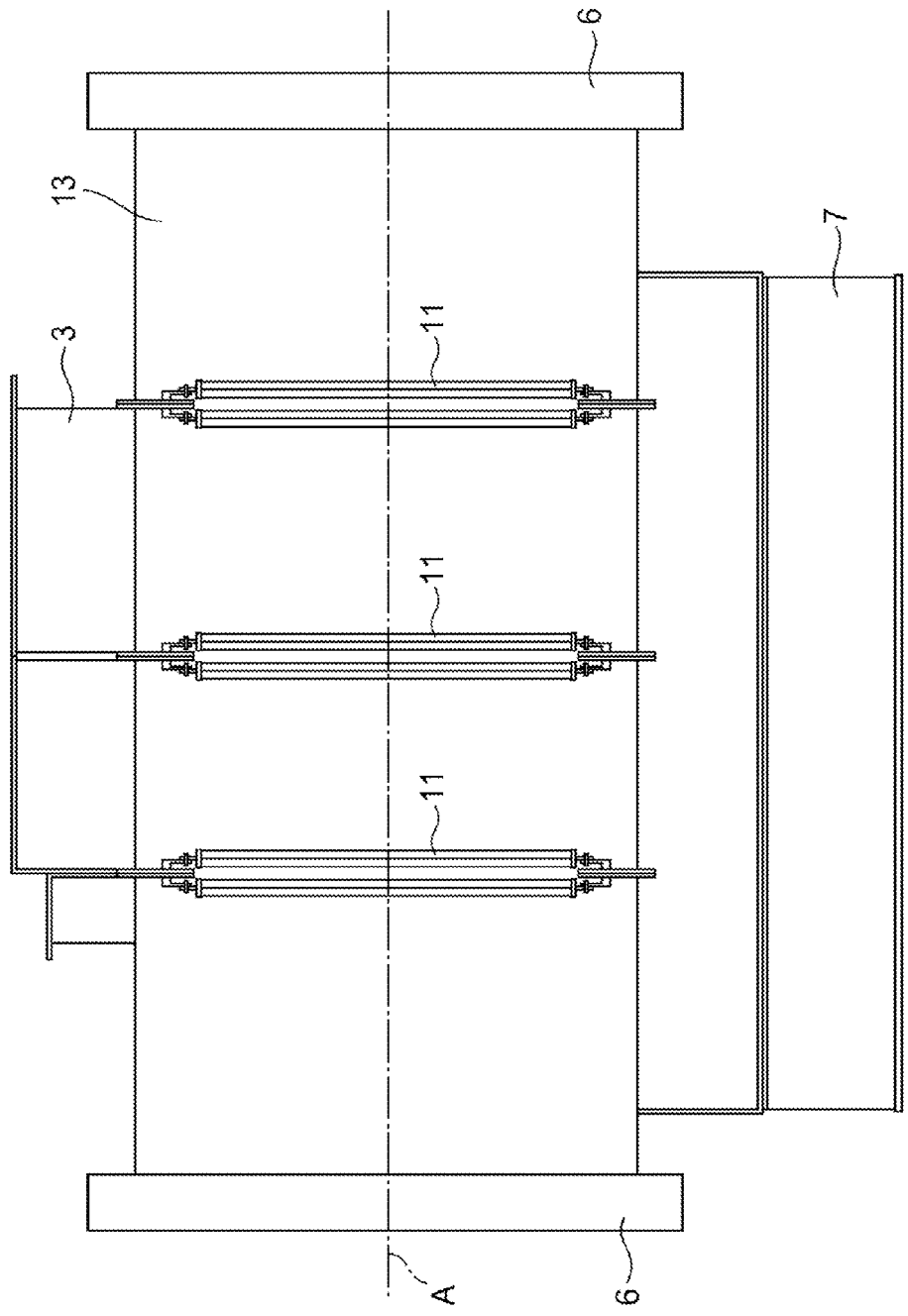
FIG. 3 is a schematic longitudinal sectional view taken in a rotational axis direction of a rotating gantry illustrated in FIG. 1.

FIG. 1 is a perspective view illustrating a particle beam treatment apparatus 20, FIG. 2 is a cross-sectional view taken in a central portion of the particle beam treatment apparatus illustrated in FIG. 1, and FIG. 3 is a schematic longitudinal sectional view taken in a rotational axis direction of a rotating gantry illustrated in FIG. 1.

In FIG. 1, the particle beam treatment apparatus 20 includes: a rotating gantry 13 that revolves and displaces an irradiation port 4 for irradiating a radiation treatment room 21 with a charged particle beam and emits an accelerated particle beam from an arbitrary position; a movement control unit 22 that moves a treatment table 5 inside of the treatment space 21 and sets a position and a direction of the treatment table 5; and an arm 23 having a proximal end supported lateral to the irradiation port 4.

The particle beam treatment apparatus 20 further includes a main body 1, a mounted magnet 2, a magnet support 3, the irradiation port 4, the treatment table 5, end rings 6, a counter weight 7, and turning rollers 8.

An inside of the main body 1 corresponds to the radiation treatment room 21. The main body 1 houses the irradiation port 4. The mounted magnet 2, the magnet support 3, and the counter weight 7 are installed outside of the main body 1. The end rings 6 connected to the main body 1 rotate in contact with the turning rollers 8 installed on a pedestal 24, whereby a patient on the treatment table 5 is irradiated with an accelerated particle beam from an arbitrary angle position.

The mounted magnet 2 is connected to the main body 1 by the magnet support 3, and has a function of guiding an accelerated particle beam to the irradiation port 4.

The counter weight 7 is a weight that is arranged at a position symmetrical to a position of the mounted magnet 2 about the rotational axis direction, that is, on a side opposite to the mounted magnet 2 with respect to the rotational axis direction, in order to maintain a weight balance of the main body 1 as a rotor.

In FIG. 2, a deformation prevention mechanism 11 is arranged on an inner surface of the main body 1 in the rotating gantry 13. The deformation prevention mechanism 11 prevents deformation caused along with a rotation of the rotating gantry 13 having a body portion whose thickness is made smaller in order to reduce a moment of inertia. The deformation prevention mechanism 11 can hold a cross-sectional shape of the main body 1 during manufacture, transportation, and a rotating operation thereof, and is formed in a horizontal bar-like shape or a horizontal and vertical cross-like shape in FIG. 2. Note that, although only one arrangement position of the deformation prevention mechanism 11 is illustrated in FIG. 2, the deformation prevention mechanisms 11 may be arranged at a plurality of positions (for example, evenly three positions) in a direction of a rotational axis A as needed, as illustrated in a schematic longitudinal sectional view taken in the rotational axis direction of the rotating gantry 13 in FIG. 3.

In order to measure a position and an acceleration of the mounted magnet 2, one or more displacement/acceleration sensors 9 are provided to the mounted magnet 2. Further, actuators or dampers 10 (10a, 10b) as control mechanisms are installed in the magnet support 3 and the deformation prevention mechanism 11. The actuator or damper 10b installed in the deformation prevention mechanism 11 is located on an axis connecting the mounted magnet 2 and a rotational axis center.

A magnet mounting position can be controlled by the actuator or damper 10a. The actuator or damper 10b installed in the deformation prevention mechanism 11 can be expanded and contracted depending on the position of the mounted magnet 2, to thereby absorb deformation of the main body 1 and control the magnet mounting position. This configuration is given as an example of the actuator or damper 10b installed in the deformation prevention mechanism 11. Alternatively, two actuators or dampers 10b may be respectively installed at positions rotationally symmetrical about the rotational axis. Still alternatively, the actuator or damper 10b may be installed in each of the deformation prevention mechanisms 11 that are arranged at a plurality of positions in the rotational axis direction, to thereby absorb more three-dimensional deformation of the main body 1 and more precisely control the magnet mounting position.

Because the magnet mounting position can be controlled by the deformation prevention mechanisms 11 and the actuators or dampers 10 in this way, rigidity of the main body 1 can be made lower, a main body plate thickness can be reduced, and a main body structure can be simplified.

Figure 4A:
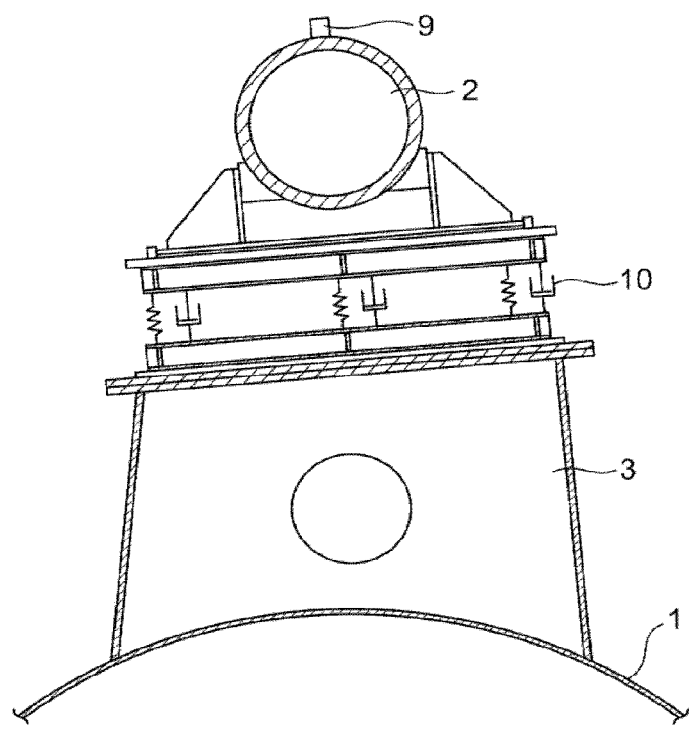
FIG. 4A is a cross-sectional view illustrating a state before correction of a mounted magnet in the embodiment of the particle beam treatment apparatus according to the present invention.
Figure 4B:
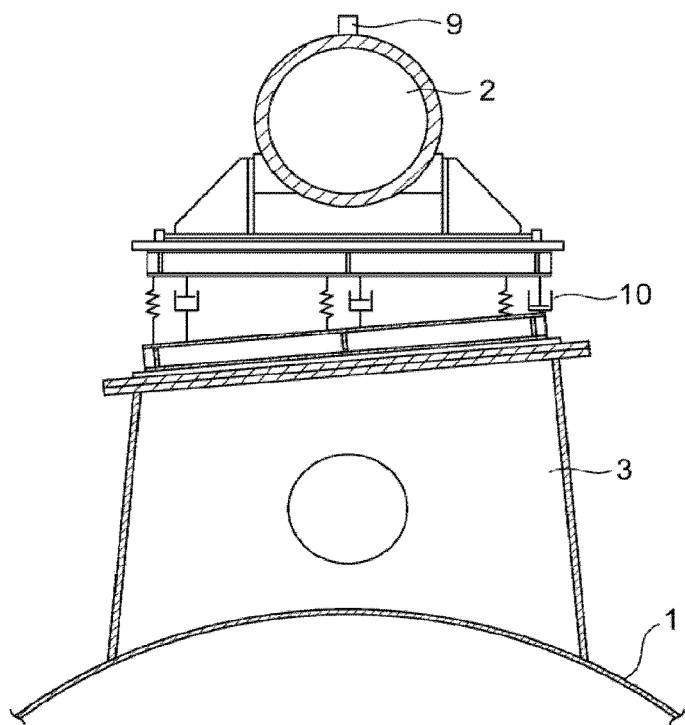
FIG. 4B is a cross-sectional view illustrating a state after the correction of the mounted magnet in the embodiment of the particle beam treatment apparatus according to the present invention.

Actions of the particle beam treatment apparatus according to the present invention are illustrated in FIGS. 4, FIG. 4A is a cross-sectional view illustrating a state before correction of the mounted magnet, and FIG. 4B is a cross-sectional view illustrating a state after the correction of the mounted magnet.

In FIG. 4A, before the correction, the position of the mounted magnet 2 is displaced from a target position along with deformation of the main body 1. Accordingly, as illustrated in FIG. 4B, with regard to the position and the acceleration of the mounted magnet 2, a current position thereof is measured by the one or more displacement/acceleration sensors 9, and a displacement between the target position and the current position is calculated with at least a single degree of freedom, for example, three-dimensionally. Then, the position and vibrations of the mounted magnet 2 are corrected and controlled by the one or more actuators or dampers 10 installed in the magnet support 3, with at least a single degree of freedom, for example, three-dimensionally.

FIG. 4 illustrate an example in which three actuators or dampers 10 are arranged on a plane perpendicular to the rotational axis. Alternatively, as illustrated in the example for the deformation prevention mechanisms 11 in FIG. 3, the actuators or dampers 10 may be arranged in a plurality of rows in the rotational axis direction, and, for example, nine actuators or dampers 10 may be arranged in three columns and three rows. As a matter of course, the position and vibrations of the mounted magnet 2 may be three-dimensionally corrected and controlled by one large actuator or damper 10.

As has been described above, according to the embodiment of the present invention, because the magnet mounting position can be controlled, rigidity of the main body can be made lower, the main body plate thickness can be reduced, and the main body structure can be simplified. Because the main body plate thickness can be reduced, a particle beam treatment apparatus having a low moment of inertia and thus being capable of making irradiation target center accuracy higher can be provided.

What is claimed is:

1. A particle beam treatment apparatus including a rotating gantry that revolves and displaces an irradiation port for irradiating a radiation treatment room provided inside of the rotating gantry with a charged particle beam, the apparatus comprising:

a gantry body portion forming the rotating gantry;
a mounted magnet;
a displacement meter or an acceleration meter; and
a control mechanism, wherein
the mounted magnet is connected to the gantry body portion with an intermediation of a magnet support, and guides the charged particle beam to the irradiation port,
the displacement meter or the acceleration meter is provided to the mounted magnet, and measures a displacement or an acceleration of the mounted magnet, and
the control mechanism controls a position of the mounted magnet in a direction so as to reduce the displacement or the acceleration with at least a single degree of freedom measured by the displacement meter or the acceleration meter.

2. The particle beam treatment apparatus according to claim 1, wherein the control mechanism that controls the position of the mounted magnet is an actuator or a damper installed in the magnet support or the gantry body portion.

3. The particle beam treatment apparatus according to claim 1, wherein a deformation prevention mechanism that holds a shape of the gantry body portion is provided on an inner surface of the gantry body portion forming the rotating gantry.

4. The particle beam treatment apparatus according to claim 3, wherein the control mechanism that controls the position of the mounted magnet is arranged in the deformation prevention mechanism.

5. The particle beam treatment apparatus according to claim 1, wherein the control mechanisms are installed at a plurality of positions in a rotational axis direction of the gantry body portion.

6. The particle beam treatment apparatus according to claim 3, wherein the deformation prevention mechanisms are installed at a plurality of positions in a rotational axis direction of the gantry body portion.

* * * * *